United States Patent [19]

Brady

[11] 4,158,655
[45] Jun. 19, 1979

[54] MONOHALOALKENYL BENZOATES AND TRIHALOALKYL BENZOATES

[75] Inventor: Donnie G. Brady, Bartlesville, Okla.

[73] Assignee: Phillips Petroleum Company, Bartlesville, Okla.

[21] Appl. No.: 540,568

[22] Filed: Jan. 13, 1975

Related U.S. Application Data

[62] Division of Ser. No. 245,387, Apr. 19, 1972, Pat. No. 3,879,445.

[51] Int. Cl.$^2$ .................. C08K 5/10; C07C 69/78
[52] U.S. Cl. ................ 260/45.75 B; 560/8; 560/59; 560/64; 560/101; 560/102; 260/45.85 R
[58] Field of Search ............ 260/45.85 R, 45.75 B; 106/15 FP; 252/8.1; 560/8, 59, 64, 101, 102

[56] References Cited

U.S. PATENT DOCUMENTS

| 2,676,946 | 4/1954 | McCurdy et al. | 260/45.75 |
|---|---|---|---|
| 2,724,643 | 11/1955 | Morris et al. | 260/45.85 |
| 3,001,954 | 9/1961 | Buchholz et al. | 260/45.85 |
| 3,151,183 | 9/1964 | Bill et al. | 260/45.85 |
| 3,236,659 | 2/1966 | Wygant et al. | 260/45.85 |
| 3,267,020 | 8/1966 | Tousignant et al. | 260/45.85 |
| 3,317,568 | 5/1967 | Wygant et al. | 260/45.85 |
| 3,401,127 | 9/1968 | Stephenson | 260/45.85 |
| 3,403,118 | 9/1968 | Listner et al. | 260/45.7 P |
| 3,600,365 | 8/1971 | Brady | 260/8.4 |
| 3,716,591 | 2/1973 | Brady | 260/648 R |

FOREIGN PATENT DOCUMENTS 2122699 12/1971 Fed. Rep. of Germany.

OTHER PUBLICATIONS

Chemical Abstracts–22480c, vol. 54.
Journal of American Chemical Society–Corey et al., vol. 89, pp. 2758 and 2759.
Textbook of Organic Chemistry–Noller, 1961, pp. 42, 43 and 44.

Primary Examiner—V. P. Hoke

[57] ABSTRACT

Monohaloalkenyl benzoates are halogenated to trihalosubstituted alkyl esters of benzoic acid. The halogenated compounds impart flame retardant properties to a variety of polymeric materials.

21 Claims, No Drawings

MONOHALOALKENYL BENZOATES AND TRIHALOALKYL BENZOATES

This application is a divisional application of Ser. No. 245,387 filed Apr. 19, 1972, now U.S. Pat. No. 3,879,445, patented Apr. 22, 1975.

FIELD OF THE INVENTION

This invention relates to halogenated compounds. In another aspect, the invention relates to flame retarded polymeric compositions.

BACKGROUND OF THE INVENTION

Flame retardancy has become a desired property for plastic articles used for commercial and household purposes, such as electrical insulation, carpeting, seat covers, and the like. Polymer compositions can be made difficultly flammable by the incorporation of various flameproofing agents. However, the ease of obtaining flame retardancy in a given polymer tends to vary from polymer to polymer. One type of polymer may be more effectively flame retarded than another, using the same amounts of additives; or, one type of polymer may require increased amounts of additives over the requirements of another type of polymer for each equivalent level of retardancy; or even one polymer species within a polymer class may require more or less flame retarded additive.

The search for novel compounds which can impart effective flame retardant properties to a variety of polymeric compositions continues.

OBJECTS OF THE INVENTION

It is an object of my invention to provide novel compositions of matter. It is a further object of my invention to provide novel halogenated organic compounds. Another object of my invention is to provide novel polymeric compositions possessing improved flame resistance.

Other objects and aspects as well as the several advantages of my invention will be apparent to those skilled in the arts to which the invention appertains from consideration of this specification including the appended claims.

BRIEF SUMMARY OF THE INVENTION

I have discovered two groups of novel compounds. Novel unsaturated monohalo compounds which I have discovered can be termed monohaloalkenylbenzoate compounds. The benzoyl moiety thereof can be substituted, and the halogen of these monohaloalkenylbenzoates is chlorine, bromine, or iodine. These monohaloalkenylbenzoates can be halogenated to novel trihalo compounds, 2,3,4-trihaloalkylbenzoate compounds, in which the additional halogen can be chlorine, bromine, or iodine, the same or different from the first halogen. The 2,3,4-trihaloalkylbenzoate compounds impart effective flame retardancy to polymeric compositions. Polymeric compositions containing the novel halogenated compounds themselves are novel.

DETAILED DESCRIPTION OF THE INVENTION

Monohaloalkenylbenzoates

The novel unsaturated monohaloalkenylbenzoate compounds can be descriptively termed 4-haloalkenyl benzoates. The compounds also can be represented by the general formula:

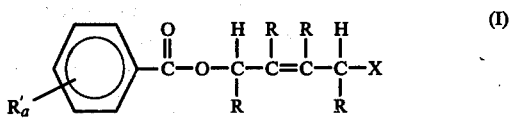

in which each R represents hydrogen or an alkyl, cycloalkyl, aryl, aralkyl, or alkaryl radical; and the halogen X is chlorine, bromine, or iodine. The R' groups on the benzene ring each represent hydrogen or a radical such as alkyl, cycloalkyl, aralkyl, alkoxy, or halogen. When R' is halogen, the halogen can be any one or more of fluorine, chlorine, bromine, or iodine. The integer indicator a can range from 0 to 5. There appears to be no particular upper limitation in the size of a particular R or R' group, as far as operability is concerned. Presently preferred compounds fall into a sub-generic group such that the total number of carbon atoms per compound does not exceed about 20. Presently further preferred is a sub-generic group of monohaloalkenyl benzoate compounds wherein a is 0, and presently most preferred are the unsubstituted benzoates in which R is hydrogen.

Examples of the 4-haloalkenyl benzoates include: 4-chloro-2-butenyl benzoate, 4-bromo-2-butenyl benzoate, 4-iodo-2-butenyl benzoate, 4-chloro-2-butenyl p-toluate, 4-chloro-2-butenyl-3,5-dimethylbenzoate, 4-chloro-3-phenyl-2-butenyl benzoate, 4-bromo-2-p-tolyl-2-butenyl 2,3,4,5-tetramethylbenzoate, 4-iodo-2-ethyl-3-phenyl-2-butenyl benzoate, 4-chloro-3-cyclohexyl-2-butenyl benzoate, 4-bromo-2-butenyl 2,4,6-tribromobenzoate, 4-chloro-2-butenyl 4-benzyl-benzoate, 4-iodo-2-butenyl 3,5-dimethoxybenzoate, 4-bromo-2,3-dimethyl-2-butenyl benzoate, 4-chloro-2-benzyl-2-butenyl 4-isopropylbenzoate, 4-iodo-2-ethyl-2-butenyl p-fluorobenzoate, 4-bromo-3-p-tolyl-2-butenyl 2,4-dichloro-benzoate, 4-chloro-2,3-diethyl-2-butenyl benzoate, 4-bromo-2-methyl-3-phenyl-2-butenyl 3,5-dibromobenzoate, 4-iodo-3-m-tolyl-2-butenyl benzoate, 4-chloro-2-butenyl 2,4,6-trimethylbenzoate, and the like, of which 4-chloro-2-butenyl benzoate is a presently preferred species.

The novel haloalkenyl esters represented by the general formula (I) can be prepared by treating an alkali metal benzoate or substituted benzoate with a 1,4-dihalo-2-alkene using a suitable catalyst such as a phosphine or quaternary phosphonium salt. The alkali metal of the alkali metal benzoate can be any of lithium, sodium, potassium, rubidium, or cesium. The benzoate radicals correspond as to substituents or lack thereof to the corresponding portion of the general formula (I) describing my novel monohalo unsaturated esters. The 1,4-dihalo-2-alkene reactant can be represented by the general formula:

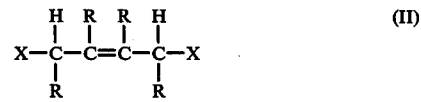

in which R and X are as previously defined. The halogens X need not be, although usually are, the same. Presently preferred are the 1,4-dihalo-2-alkenes in which each R is hydrogen, such as 1,4-dihalo-2-butene, presently preferred being 1,4-dichloro-2-butene, 1,4-diiodo-2-butene, and 1,4-dibromo-2-butene. Various 1,4- dihalo-2-butenes can be readily prepared by halogenation of 1,3-butadiene or substituted 1,3-butadienes according to processes well known in the arts. Other examples of 1,4-dihalo-2-alkene reactants include: 1,4-dichloro-2-phenyl-2-butene, 1,4-dibromo-2-methyl-2-butene, as well as others corresponding to the appropriate moieties for the described 4-haloalkenyl benzoates without repetitious listing, and the like.

Phosphine or phosphonium salt catalysts include those which can be represented by the general formulae $R_3'''P$ or $(R_4'''P)_mY$. The integer designator m can range from 1 to 3, and m is equal to the valence of Y. Y can be any anionic group with appropriate valence useful in quaternary phosphonium compounds as catalysts. $R'''$ represents various hydrocarbon radicals such as alkyl, cycloalkyl, aryl, or any combination thereof, containing up to about 10 carbon atoms per $R'''$ group, although this is governed by availability of materials rather than effectiveness or suitability. Examples of suitable phosphines include trimethyl phosphine, trioctyl phosphine, tricyclopentyl phosphine, triphenyl phosphine, tribenzyl phosphine, butylcyclohexylphenyl phosphine, and the like. Examples of quaternary phosphonium salts include ethyltriphenylphosphonium benzoate, tetraethylphosphonium acetate, tetraoctylphosphonium octanoate, tetra(4-tolyl)phosphonium 4-toluate, ethyltriphenylphosphonium chloride or fluoride or bromide, or any of the equivalent cyanide, cyanate, isocyanate, sulfate, phosphate, sulfonate, and the like quaternary phosphonium salts.

From about 0.1 to 50 moles or more of catalyst can be employed per 100 moles of alkali metal carboxylate employed in the reaction, although a range of about 0.5 mole to 10 moles presently is preferred.

As can be observed from consideration of the reaction, the equivalent ratio of the 1,4-dihalo-2-alkene to the alkali metal benzoate is 1:1, although a broad range can be employed of up to about 500:1 or even more, with a presently preferred range of about 2:1 to 10:1. It appears desirable to employ an excess of 1,4-dihalo-2-alkene reactant in order to maximize yields of the desired haloalkenylbenzoate ester.

In general, any convenient contacting temperatures can be employed depending on the particular reactants and general reaction parameters. An exemplary temperature would be a range of about 50° C. to 200° C. Pressure preferably should be sufficient to maintain the reactants substantially in a liquid phase, such as from about 0.5 atmosphere to 10 atmospheres, depending to some extent on temperatures and diluents employed. Reaction times sufficient to effect the degree of conversion desired should be employed, and range from a few minutes to upwards of 48 hours or more.

The treating of the alkali metal benzoate with the 1,4-dihalo-2-alkene using the above-described catalysts presently preferably employs substantially anhydrous conditions, although minor traces of water often associated with the reactants do not interfere unduly.

The use of a diluent is a convenience, although the reaction can be carried out in excess 1,4-dihalo-2-alkene such that the 1,4-dihalo-2-alkene then acts both as reactant and as reaction medium or diluent, thus avoiding the use of an extraneous material. Examples of suitable diluents include acetone, methyl ethyl ketone, methyl isobutyl ketone, tetrahydropyran, cyclohexanone; any of the aromatic solvent hydrocarbons such as benzene, toluene, xylenes, and the like; aliphatic hydrocarbons such as pentane, hexane, and octane; tetrahydrofuran, N,N-dimethylformamide, cyclododecanone, N-methylpyrrolidone, and the like, alone, or in admixture with each other.

The resulting 4-haloalkenyl esters can be recovered by stripping, solvent extraction, distillation, and the like, as necessary or convenient.

Trihaloalkyl Benzoates

The novel unsaturated monohalo esters of my invention are used to prepare novel 2,3,4-trihaloalkyl esters of benzoic acid which are a further part of my invention. The 2,3,4-trihaloalkyl esters of benzoic acid can be represented by the general formula:

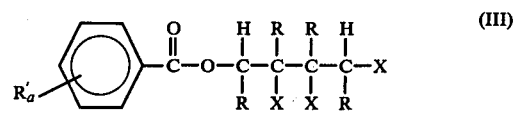

wherein R, R', a and X, are as defined hereinbefore, with the halogens in the two- and three-position being the same.

The novel 2,3,4-trihaloalkyl benzoates conveniently are prepared by the addition of halogen to the corresponding 4-halolkenyl esters. Such halogenation can be carried out at moderate temperatures, i.e., from about −20° to +50° C., using a solvent such as chloroform, carbon tetrachloride, carbon disulfide, or the like, under halogenation conditions convenient for halogenation of unsaturated materials. A reaction interval of several minutes to several hours, such as from 1 hours to 12 hours, should be sufficient. If desired, a minor trace of hydrogen halide can be added as a catalyst, or a mixture of halogen and aluminum halide in an alcohol such as ethanol can be used. Generally an excess of halogen is avoided, so that a 1:1 molar ratio of halogen to unsaturated benzoate presently would be preferred. Examples of the novel trihalobenzoates include any of the hereinbefore described 4-haloalkenyl benzoates which have been halogenated so as to add halogen to the double bond to become trihaloalkyl benzoates, such as 4-chloro-2-butenyl benzoate to 2,3-dibromo-4-chlorobutyl benzoate, without needlessly repeating a list of exemplary species.

Flameproofed Polymer Compositions

The novel trihalo compounds of my invention are useful as flame retardant additives for polymeric compositions. These additives can be employed, for example, in compositions of thermoplastic polymers.

Suitable polymers include any of the thermoplastic polymeric compositions such as the polydienes, i.e., the homopolymers and copolymers of conjugated dienes having from 4 to 10 carbon atoms per molecule, such as butadiene, piperylene, isoprene, chloroprene, 1,5-hexadiene, and the like, including copolymers with monovinyl-substituted aromatic compounds of up to 12 carbon atoms per molecule. Presently of importance because of wide textile usage are polymers of the aliphatic 1-monoolefins known generally as polymonoolefins. These polymers include homopolymers and copolymers of aliphatic 1-monoolefins having at least 2 carbon atoms per molecule, usually 2 to 8 carbon atoms for commercial availability, such as polyethylene, polypropylene, copolymers of ethylene and propylene, or copolymers of such monomers with minor amounts of monomers copolymerizable therewith such as ethylene, propylene, 1-butene, 1-hexene, 1-octene, monovinyl-substituted aromatic compounds of up to 12 carbon atoms such as styrene, alpha-vinyl naphthalene, p-isopropyl styrene, p-methyl styrene, and the like. Other polymeric substances employing flame retardants include a wide variety of other polymers such as the poly(vinyl halides) such as poly(vinyl chloride); cellulose; acrylic resins; and the like.

The trihaloalkyl esters of my invention should be employed in polymer compositions in such minor amounts as are effective in providing the desired degree of flame retardancy to the particular polymer or in the polymeric composition involved, which amount can vary over a broad range, depending on the polymer characteristics and the degree of protection desired or required. The presently preferred range of additive is about 3 to 30 parts per 100 parts of polymer, presently more preferred in an amount within the range of 5 to 10 parts, excluding other additives, fillers, colorants, and the like.

Antimony oxide, presently preferred as the trioxide, can be employed with halogenated additives to enhance the effectiveness of organic flame retardants, such as from about 0.5 to 20 parts of antimony trioxide per 100 parts of polymer. A typical weight ratio of halogenated additive to antimony oxide would be about 0.1:1 to 10:1, presently preferred about 2:1. Other useful oxides include bismuth oxide and arsenic trioxide which can be used, if desired, in place of or even with the antimony trioxide for this purpose.

EXAMPLES

The examples and runs described herein are intended to illustrate my invention. Particular components described and conditions employed should be considered illustrative and not limitative of the reasonable scope and extent of my invention.

EXAMPLE I

To a dry stirred autoclave were added sodium benzoate 20 g, 0.14 mole, ethyltriphenylphosphonium bromide 1.2 g, 0.003 mole, and 1,4-dichloro-2-butene 37.5 g, 0.30 mole, in 50 ml of 2-butanone. The system was flushed with dry nitrogen. The stirred mixture was heated to 110° C., held at this temperature for 2.5 hours, then cooled to room temperature. The solid material was filtered off, washed with 25 ml of 2-butanone, and air dried to give 8.8 g residue (8.2 g of NaCl theoretical).

The solvent in the filtrate was removed in vacuo to leave 43 g of a yellow liquid. Ether was added and the resulting tan solid removed by filtration and shown to be ethyltriphenylphosphonium bromide by infrared analysis.

The etheral filtrate was washed with 100 ml of distilled water and the organic layer was separated and dried over anhydrous magnesium sulfate. The ether was removed in vacuo to give a yellow liquid. Unreacted 1,4-dichloro-2-butene was removed by distillation b.p.ca. 60° C./20 mm. Fractionation of the remaining liquid gave 16 g of ester isolated as a clear colorless oil b.p. 100° C./0.1 mm. This liquid was shown by NMR analysis to be 4-chloro-2-butenyl benzoate.

EXAMPLE II

To a stirred reactor was added a solution of the 4-chloro-2-butenyl benzoate 10 g, 0.0475 mole in 60 ml of chloroform. A small amount of sodium bicarbonate was added and the stirred mixture cooled in an ice-salt bath. To this was added slowly over about nine hours a solution of bromine 7.6 g, 0.0475 mole, aluminum chloride 0.15 g, 0.001 mole, and absolute ethanol 1 ml, in 25 ml of chloroform. Since the bromine reaction was slow the solution was allowed to warm to room temperature. The resulting straw colored solution was stirred overnight at room temperature. The solution was washed with distilled water, 5 percent aqueous sodium bicarbonate, and again with distilled water. The organic layer was separated, dried over anhydrous magnesium sulfate, and concentrated in vacuo to leave 16.9 g of a colorless oil. Infrared and NMR spectra of this oil indicated it to be 2,3-dibromo-4-chlorobutyl benzoate.

EXAMPLE III

The following data demonstrate the flame retarding properties of the 2,3-dibromo-4-chlorobutyl benzoate in a polymer composition. Polypropylene was compounded with varying amounts of the trihalobenzoate and with antimony trioxide, the latter frequently employed to assist flame retarding effects of halogenated compounds, although by itself it exhibits no such properties.

TABLE I

| Benzoate, phr | Sb$_2$O$_3$, phr | Limiting Oxygen Index ASTM D-2863 | ASTM D-635 |
|---|---|---|---|
| 2 | 1 | 21.5 | burned |
| 3 | 1.5 | 23.4 | burned |
| 5 | 2.5 | 24.5 | self-extinguishing to nonburning |

These data demonstrate that the trihalobenzoates can be used for effective flame retarding in polymeric composition.

The polymeric compositions of my invention using the novel flame retardant can be compounded with other additives such as thermal stabilizers, fillers, pigments, dyes, plasticizers, and the like, any or all of which can be added to the formulation to improve stability and/or other properties of the final polymer composition for various purposes.

Reasonable variations and modifications of my invention are possible while still within the scope of my disclosure, and without departing from the intended scope and spirit thereof, as detailed in my specification and the claims appended.

I claim:

1. A flame retarded polymeric composition incorporating at least one poly(1-monoolefin) polymer together with an effective flame-retarding amount of at least one 2,3,4-trihaloalkyl ester of benzoic acid represented by the general formula

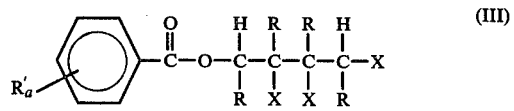

wherein each R represents hydrogen or a radical which is alkyl, cycloalkyl, aryl, aralkyl, or alkaryl; X is chlorine, bromine, or iodine; each R' is individually selected from hydrogen, alkyl, X or fluorine; a is 5; wherein the total number of carbon atoms per 2,3,4-trihaloalkyl ester of benzoic acid does not exceed 20; and wherein the halogen in the 2- and 3-position are the same.

2. The flame retarded polymeric composition according to claim 1 wherein said 2,3,4-trihaloalkyl ester of benzoic acid is selected from the group consisting of 2,3-dihalo-4-chlorobutyl benzoate, 2,3-dihalo-4-bromobutyl benzoate, 2,3-dihalo-4-iodobutyl benzoate, 2,3-dihalo-4-chlorobutyl-p-toluate, 2,3-dihalo-4-chlorobutyl 3,5-dimethylbenzoate, 2,3-dihalo-4-chloro-3-phenylbutyl benzoate, 2,3-dihalo-4-bromo-2-p-tolylbutyl 2,3,4,5-tetramethylbenzoate, 2,3-dihalo-4-iodo-2-ethyl-3-phenylbutyl benzoate, 2,3-dihalo-4-chloro-3-cyclohexylbutyl benzoate, 2,3-dihalo-4-bromobutyl 2,4,6-tribromobenzoate, 2,3-dihalo-4-bromo-2,3-dimethylbutyl benzoate, 2,3-dihalo-4-chloro-2-benzylbutyl 4-isopropylbenzoate, 2,3-dihalo-4-iodo-2-ethylbutyl 4-fluorobenzoate, 2,3-dihalo-4-bromo-3-p-tolybutyl 2,4-dichlorobenzoate, 2,3-dihalo-4-chloro-2,3-diethylbutyl benzoate, 2,3-dihalo-4-bromo-2-methyl-3-phenylbutyl 3,5-dibromobenzoate, 2,3-dihalo-4-iodo-3-m-tolylbutyl benzoate, and 2,3-dihalo-4-chlorobutyl 2,4,6-trimethylbenzoate.

3. The flame retarded polymeric composition according to claim 1 wherein in said 2,3,4-trihaloalkyl ester of benzoic acid said R' is hydrogen.

4. The flame retarded polymeric composition according to claim 3 wherein in said 2,3,4-trihaloalkyl ester of benzoic acid said R is hydrogen.

5. The flame retarded polymeric composition according to claim 4 wherein in said 2,3,4-trihaloalkyl ester of benzoic acid said X is chlorine or bromine.

6. The flame retarded polymeric composition according to claim 5 wherein in said 2,3,4-trihaloalkyl ester of benzoic acid each X in the 2- and 3-position is bromine, and X in the 4-position is chlorine, and the species is 2,3-dibromo-4-chlorobutylbenzoate.

7. The flame retarded polymeric composition according to claim 1 wherein said minor effective flame-retarding amount of said ester is about 3 to 30 parts of ester per 100 parts polymer excluding other additives, and said flame retarded polymeric composition further incorporates about 0.5 to 20 parts by weight of antimony oxide per 100 parts of polymer excluding other additives.

8. The flame retarded polymeric composition according to claim 7 wherein said polymer is a polypropylene.

9. The flame retarded polymeric composition according to claim 8 wherein said ester is 2,3-dibromo-4-chlorobutylbenzoate.

10. 2,3,4-trihaloalkyl esters of benzoic acid represented by the general formula

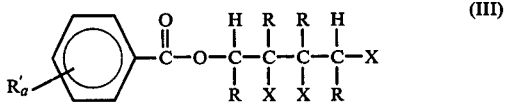
(III)

in which each R' is selected from the group consisting of cycloalkyl, aralkyl, alkoxy, and hydrogen, such that at least one R' is said cycloalkyl, aralkyl, or alkoxy; X is halogen, and is chlorine, bromine, or iodine; R is hydrogen or a radical which is alkyl, cycloalkyl, aryl, aralkyl, or alkaryl; a is an integer and is 5; and wherein the halogens in the 2 and 3 position are the same.

11. The 2,3,4-trihaloalkyl esters of benzoic acid according to claim 10, wherein R is hydrogen.

12. The 2,3,4-trihaloalkyl esters of benzoic acid according to claim 11, wherein X is chlorine or bromine.

13. The 2,3,4-trihaloalkyl esters of benzoic acid according to claim 12 wherein each X in the 2 and 3 position is bromine and X in the 4 position is chlorine.

14. The 2,3,4-trihaloalkyl esters of benzoic acid and substituted benzoic acids according to claimm 8 selected from the group consisting of 2,3-dihalo-4-iodobutyl 3,5-dimethyoxybenzoate, or 2,3-dihalo-4-chlorobutyl 4-benzylbenzoate.

15. A flame retarded polymeric composition incorporating at least one poly(1-momoolefin) together with an effective flame-retarding amount of at least one 2,3,4-trihaloalkyl ester of benzoic acid represented by the general formula

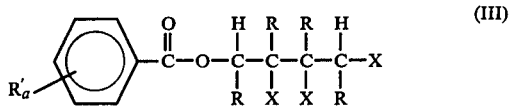
(III)

wherein each R' is hydrogen or a radical selected from the group consisting of alkyl, cycloalkyl, aralkyl, alkoxy, X or fluorine; R is hydrogen or a radical selected from the group consisting of alkyl, cycloakly, aryl, aralkyl, or alkaryl; X is halogen and is chlorine, bromine, or iodine; a is an integer and is 5; and wherein the halogens in the 2 and 3 position are the same; and wherein the total number of carbon atoms per compound does not exceed about 20.

16. The polymeric composition according to claim 15 wherein said poly(1-monoolefin) is a polymer or copolymer of aliphatic 1-monoolefins of 2 to 8 carbon atoms per molecule.

17. The polymeric composition according to claim 15 wherein said 2,3,4-trihaloalkyl esters of benzoic acid is selected from the group consisting of 2,3-dihalo-4-chlorobutyl benzoate, 2,3-dihalo-4-bromobutyl benzoate, 2,3-dihalo-4-iodobutyl benzoate, 2,3-dihalo-4-chlorobutyl p-toluate, 2,3-dihalo-4-chlorobutyl 3,5-dimethylbenzoate, 2,3-dihalo-4-chloro-3-phenylbutyl benzoate, 2,3-dihalo-4-bromo-2-p-tolylbutyl 2,3,4,5-tetramethylbenzoate, 2,3-dihalo-4-iodo-2-ethyl-3-phenylbutyl benzoate, 2,3-dihalo-4-chloro-3-cyclohexylbutyl benzoate,
2,3-dihalo-4-bromobutyl,
2,4,6-tribromobenzoate, 2,3-dihalo-4-bromo-2,3-dimethylbutyl benzoate,
2,3-dihalo-4-chloro-2-benzylbutyl 4-isopropylbenzoate,
2,3-dihalo-4-iodo-2-ethylbutyl 4-fluorobenzoate,
2,3-dihalo-4-bromo-3-p-tolylbutyl 2,4-dichlorobenzoate,
2,3-dihalo-4-chloro-2,3-diethylbutyl benzoate,
2,3-dihalo-4-bromo-2-methyl-3-phenylbutyl 3,5-dibromobenzoate,
2,3-dihalo-4-iodo-3-m-tolylbutyl benzoate, and
2,3-dihalo-4-chlorobutyl 2,4,6-trimethylbenzoate.

18. The polymeric composition according to claim 15 wherein in said 2,3,4-trihaloalkyl esters of benzoic acid R' is hydrogen, R is hydrogen, and wherein said effective minor flame-proofing amount is from about 3 to 30 parts of ester per 100 parts of polymer excluding other additives.

19. The polymeric composition according to claim 18 further incorporating into said polymeric composition at least one of antimony oxide, bismuth oxide, or arsenic oxide, in an amount sufficient to provide from about 0.5 to 20 parts of said oxide per 100 parts of polymer excluding other additives.

20. The polymeric composition according to claim 19 wherein said oxide is antimony oxide, and wherein is employed a weight ratio of 2,3,4-trihaloalkyl esters of benzoic acid: antimony oxide of about 0.1:1 to 10:1.

21. A polymeric composition according to claim 20 wherein said polymer is polypropylene, and said ester is 2,3-dibromo-4-chlorobutylbenzoate.

* * * * *